United States Patent
Wang et al.

(10) Patent No.: US 8,563,747 B2
(45) Date of Patent: Oct. 22, 2013

(54) PROCESSES FOR THE ALKYLATION OF PYRAZOLES

(75) Inventors: Linhua Wang, Greensboro, NC (US); Jefferson Thomas Ebert, Greensboro, NC (US)

(73) Assignee: Syngenta Crop Protection, LLC, Greensboro, NC (US)

( * ) Notice: Subject to any disclaimer, the term of this patent is extended or adjusted under 35 U.S.C. 154(b) by 0 days.

(21) Appl. No.: 13/388,246

(22) PCT Filed: Jul. 27, 2010

(86) PCT No.: PCT/EP2010/060884
§ 371 (c)(1),
(2), (4) Date: Jan. 31, 2012

(87) PCT Pub. No.: WO2011/012620
PCT Pub. Date: Feb. 3, 2011

(65) Prior Publication Data
US 2012/0130085 A1   May 24, 2012

Related U.S. Application Data

(60) Provisional application No. 61/230,134, filed on Jul. 31, 2009, provisional application No. 61/361,570, filed on Jul. 6, 2010.

(51) Int. Cl.
*C07D 231/14* (2006.01)
*C07D 409/12* (2006.01)

(52) U.S. Cl.
USPC ..................... 548/365.7; 548/374.1

(58) Field of Classification Search
None
See application file for complete search history.

(56) References Cited

U.S. PATENT DOCUMENTS 5,498,624 A * 3/1996 McLoughlin et al. ........ 514/406
7,678,924 B2 * 3/2010 Walter et al. ............... 548/374.1

FOREIGN PATENT DOCUMENTS

| JP | 2000044541 | 2/2000 |
|---|---|---|
| WO | 95/25099 | 9/1995 |
| WO | 2005/123690 | 12/2005 |
| WO | 2006/045504 | 5/2006 |
| WO | 2007/048556 | 5/2007 |
| WO | 2007/071900 | 6/2007 |
| WO | 2008/053044 | 5/2008 |
| WO | 2008/141020 | 11/2008 |

OTHER PUBLICATIONS

Tarrago G et al: "Orientation de la Reaction D'Alkylation des Pyrazoles dans des Conditions Neutres et en Catalyse par Transfer de Phase", Journal of Heterocyclic Chemistry, Wiley-Blackwell Publishing, Inc., US, vol. 17, No. 1, Jan. 1, 1980, pp. 137-142.

* cited by examiner

*Primary Examiner* — Kamal Saeed
(74) *Attorney, Agent, or Firm* — R. Kody Jones

(57) ABSTRACT

The invention provides a process for the preparation of a compound of formula (I) in particular, wherein a compound of formula (II) is reacted with a dialkylsulphate. $R^1$ is $C_1$-$C_4$haloalkyl; $R^2$ is optionally substituted alkyl, optionally substituted aryl or optionally substituted heteroaryl; and $R^3$ is methyl or ethyl.

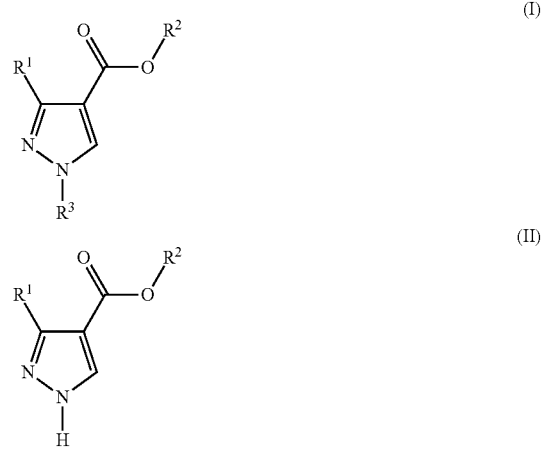

22 Claims, No Drawings

PROCESSES FOR THE ALKYLATION OF PYRAZOLES

This application is a 371 of International Application No. PCT/EP2010/060884 filed Jul. 27, 2010, which claims priority to U.S. 61/230,134 filed Jul. 31, 2009, and U.S. 61/361,570 filed Jul. 6, 2010, the contents of which are incorporated herein by reference.

The present invention relates to processes for the regioselective N-alkylation of substituted pyrazoles and to the use of alkylsulphonates in the regioselective N-alkylation of substituted pyrazoles.

N-alkylated substituted pyrazoles, for example ethyl 3-(difluoromethyl)-1-methyl-1H-pyrazole-4-carboxylate (DFPE), are valuable intermediates in the preparation of fungicides, as described, for example, in WO 03/074491.

According to WO 95/25099, N-alkylated substituted pyrazoles can be prepared by reacting the corresponding substituted pyrazoles with alkyl halides under basic conditions. The use of alkyl halides in the N-alkylation of substituted pyrazoles is problematic, however, on account of their toxic properties. Furthermore, those compounds are expensive and, in addition, exhibit only a low degree of regioselectivity—in respect of the two nitrogen atoms of the pyrazole ring. For those reasons, such processes are particularly unsuitable for large-scale preparation of N-alkylated substituted pyrazoles.

According to JP-2000-044541, N-alkylated substituted pyrazoles can be prepared by reacting the corresponding substituted pyrazoles with carboxylic acid dialkyl esters, with addition of a base. The use of carboxylic acid dialkyl esters is not desirable, because those compounds are of low reactivity. Furthermore, the regioselectivity of such N-alkylation is generally dependent upon the chemical nature of the substituents on the pyrazole ring, so that N-alkylations using carboxylic acid dialkyl esters in some cases exhibit unsatisfactory regioselectivity.

According to WO 2006/045504 N-alkylated substituted pyrazoles can be prepared regioselectively by reacting the corresponding substituted pyrazoles with trialkyl phosphates.

There is a continuing need to find improved processes for preparing DFPE on a commercial scale which starts from easily and inexpensively obtainable starting materials.

The present invention relates to a process for the preparation of compounds of formula I:

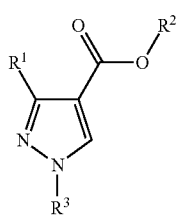

(I)

wherein $R^1$ is $C_1$-$C_4$haloalkyl;
$R^2$ is optionally substituted alkyl, optionally substituted aryl or optionally substituted heteroaryl; and
$R^3$ is methyl or ethyl;

wherein a compound of formula II:

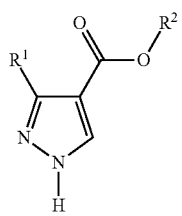

(II)

wherein $R^1$ and $R^2$ are as defined for the compound of formula I;
is reacted with a compound of formula III:

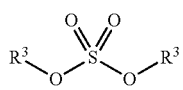

(III)

wherein $R^3$ is as defined for the compound of formula I.

The alkyl groups appearing in the above substituent definitions may be straight-chain or branched. For example an alkyl group may be methyl, ethyl, n-propyl, isopropyl, n-butyl, sec-butyl, isobutyl or tert-butyl, preferably methyl or ethyl. Halogen is generally fluorine, chlorine, bromine or iodine, preferably fluorine. $C_1$-$C_4$ haloalkyl groups are derived from the mentioned $C_1$-$C_4$alkyl groups and are preferably difluoromethyl or trifluoromethyl.

Aryl refers to aromatic hydrocarbon ring systems which may be a single ring or multiple rings which are fused together or linked covalently. Examples for aryl groups are phenyl, naphthyl, tetrahydronaphthyl, indanyl, indenyl, anthracenyl, phenanthrenyl and biphenyl.

Heteroaryl refers to aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

$R^2$ may be optionally substituted alkyl, optionally substituted aryl or optionally substituted heteroaryl. This means that the alkyl, aryl and heteroaryl groups may or may not carry one or more identical or different substituents. Normally not more than three substituents are present at the same time. Examples of substituents are: halogen, alkyl, haloalkyl, cycloalkyl, cycloalkylalkyl, alkenyl, haloalkenyl, cycloalkenyl, alkynyl, haloalkynyl, alkoxy, haloalkoxy, cycloalkoxy, alkenyloxy, haloalkenyloxy, alkynyloxy, haloalkenyloxy, alkylthio, haloalkylthio, cycloalkylthio, alkenylthio, alkynylthio, alkylcarbonyl, haloalkylcarbonyl, cycloalkylcarbonyl, alkenylcarbonyl, alkynylcarbonyl, alkoxyalkyl, cyano, nitro, hydroxy, mercapto, amino, alkylamino and dialkylamino.

Preferred optional substituents are $C_1$-$C_8$ alkyl, halo-$C_1$-$C_8$ alkyl, $C_3$-$C_8$ cycloalkyl, $C_3$-$C_8$cycloalkyl-$C_1$-$C_8$alkyl, $C_2$-$C_8$ alkenyl, halo-$C_2$-$C_8$ alkenyl, $C_3$-$C_8$ cyclo-$C_2$-$C_8$ alkenyl, $C_2$-$C_8$ alkynyl, halo-$C_2$-$C_8$ alkynyl, $C_1$-$C_8$ alkoxy, halo-$C_1$-$C_8$ alkoxy, $C_3$-$C_8$ cycloalkoxy, $C_2$-$C_8$ alkenyloxy, halo-$C_2$-$C_8$ alkenyloxy, $C_2$-$C_8$ alkynyloxy, halo-$C_2$-$C_8$ alkenyloxy, $C_1$-$C_8$ alkylthio, halo-$C_1$-$C_8$ alkylthio, $C_3$-$C_8$ cycloalkylthio, $C_2$-$C_8$ alkenylthio, $C_2$-$C_8$ alkynylthio, $C_1$-$C_8$ alkylcarbonyl, halo-$C_1$-$C_8$ alkylcarbonyl, $C_3$-$C_8$ cycloalkylcarbonyl, $C_2$-$C_8$ alkenylcarbonyl, $C_2$-$C_8$ alkynylcarbonyl, $C_1$-$C_8$ alkoxy-$C_1$-$C_8$ alkyl, cyano, nitro, hydroxy, mercapto, amino, $C_1$-$C_8$ alkylamino and $C_1$-$C_8$ dialkylamino.

More preferred optional substituents are $C_1$-$C_4$ alkyl, halo-$C_1$-$C_4$ alkyl, $C_3$-$C_6$ cycloalkyl, $C_3$-$C_6$cycloalkyl-$C_1$-$C_4$alkyl, $C_2$-$C_4$ alkenyl, halo-$C_2$-$C_4$ alkenyl, $C_3$-$C_6$ cyclo-$C_2$-$C_4$ alkenyl, $C_2$-$C_4$ alkynyl, halo-$C_2$-$C_4$ alkynyl, $C_1$-$C_4$ alkoxy, halo-$C_1$-$C_4$ alkoxy, $C_3$-$C_6$ cycloalkoxy, $C_2$-$C_4$ alkenyloxy, halo-$C_2$-$C_4$ alkenyloxy, $C_2$-$C_4$ alkynyloxy, halo-$C_2$-$C_4$ alkenyloxy, $C_1$-$C_4$ alkylthio, halo-$C_1$-$C_4$ alkylthio, $C_3$-$C_6$ cycloalkylthio, $C_2$-$C_4$ alkenylthio, $C_2$-$C_4$ alkynylthio, $C_1$-$C_4$ alkylcarbonyl, halo-$C_1$-$C_4$ alkylcarbonyl, $C_3$-$C_6$ cycloalkylcarbonyl, $C_2$-$C_4$ alkenylcarbonyl, $C_2$-$C_4$ alkynylcarbonyl, $C_1$-$C_4$ alkoxy-$C_1$-$C_4$ alkyl, cyano, nitro, hydroxy, mercapto, amino, $C_1$-$C_4$ alkylamino and $C_1$-$C_4$ dialkylamino.

Even more preferred optional substituents are $C_1$-$C_4$ alkyl, $C_1$-$C_4$ haloalkyl, $C_1$-$C_4$ alkoxy, halo-$C_1$-$C_4$ alkoxy, halogen, hydroxy, cyano, nitro, and amino.

Typical examples for optionally substituted aryl include 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2-cyanophenyl, 3-cyanophenyl, 4-cyanophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3-dicyanophenyl, 2,4-dicyanophenyl, 2,5-dicyanophenyl, 2,6-dicyanophenyl, 3,4-dicyanophenyl, 3,5-dicyanophenyl, 2,3-bis(trifluoromethyl)phenyl, 2,4-bis(trifluoromethyl)phenyl, 2,5-bis(trifluoromethyl)phenyl, 2,6-bis(trifluoromethyl)phenyl, 3,4-bis(trifluoromethyl)phenyl, 3,5-bis(trifluoromethyl)phenyl, 2,3-bis(trifluoromethoxy)phenyl, 2,4-bis(trifluoromethoxy)phenyl, 2,5-bis(trifluoromethoxy)phenyl, 2,6-bis(trifluoromethoxy)phenyl, 3,4-bis(trifluoromethoxy)phenyl, 3,5-bis(trifluoromethoxy)phenyl, 2-chloro-5-fluorophenyl, 2-fluoro-5-methylphenyl, 2-fluoro-5-methoxyphenyl, 5-chloro-2-fluorophenyl, 2-chloro-5-methylphenyl, 2-chloro-5-methoxyphenyl, 5-fluoro-2-methylphenyl, 5-chloro-2-methylphenyl, 5-methoxy-2-methylphenyl, 5-fluoro-2-methoxyphenyl, 5-chloro-2-methoxyphenyl and 2-methoxy-5-methylphenyl.

Typical examples for optionally substituted heteroaryl include 5-methyl-3-trifluoromethylpyrazol-1-yl, 3-methyl-5-trifluoromethylpyrazol-1-yl, 3,5-bis-trifluoromethylpyrazol-1-yl, 3,5-dimethylpyrazol-1-yl, 5-ethyl-3-trifluoromethylpyrazol-1-yl, 5-methyl-3-trifluoromethoxypyrazol-1-yl, 2-methyl-4-trifluoromethylimidazol-1-yl, 4-methyl-2-trifluoromethylimidazol-1-yl, 2,4-bis-trifluoromethylimidazol-1-yl, 2,4-dimethylimidazol-1-yl, 2-ethyl-4-trifluoromethylimidazol-1-yl, 2-methyl-4-trifluoromethoxyimidazol-1-yl, 5-methyl-3-trifluoromethyl[1,2,4]triazol-1-yl, 3-methyl-5-trifluoromethyl[1,2,4]triazol-1-yl, 3,5-bis-trifluoromethyl[1,2,4]triazol-1-yl and 3,5-dimethyl[1,2,4]triazol-1-yl, 5-ethyl-3-trifluoromethyl[1,2,4]triazol-1-yl, 5-methyl-3-trifluoromethoxy[1,2,4]triazol-1-yl.

Alkoxy on its own or as part of another substituent is, depending upon the number of carbon atoms mentioned, for example methoxy, ethoxy, 1-propoxy, 2-propoxy, n-butoxy, 2-n-butoxy, or 2-tert-butoxy.

Alkenyl on its own or as part of another substituent is, depending upon the number of carbon atoms mentioned, for example, ethenyl, allyl, propen-1-yl, buten-2-yl, buten-3-yl, penten-1-yl, penten-3-yl, hexen-1-yl or 4-methyl-penten-3-yl.

Alkynyl on its own or as part of another substituent is, depending upon the number of carbon atoms mentioned, for example, ethynyl, propyn-1-yl, propyn-2-yl, butyn-1-yl, butyn-2-yl, 1-methyl-2-butynyl, hexyn-1-yl or 1-ethyl-2-butynyl.

Preferably, $R^1$ is difluoromethyl or trifluoromethyl;

Preferably $R^2$ is $C_1$-$C_8$ alkyl, phenyl, or phenyl-$C_1$-$C_8$ alkyl, wherein the alkyl, phenyl and phenylalkyl are each optionally substituted with one or more of, e.g. 1 to 3, $C_1$-$C_4$ alkyl, $C_1$-$C_4$ haloalkyl, $C_1$-$C_4$ alkoxy, halo-$C_1$-$C_4$ alkoxy, halogen, hydroxy, cyano, nitro and amino. More preferably $R^2$ is $C_1$-$C_8$ alkyl or $C_1$-$C_8$ haloalkyl, phenyl or benzyl, wherein the phenyl and benzyl are each optionally substituted with halogen, e.g. 1 to 3 halogen atoms. More preferably $R^2$ is $C_1$-$C_6$ alkyl. Even more preferably $R^2$ is $C_1$-$C_4$ alkyl. Most preferably $R^2$ is methyl or ethyl.

Preferably $R^3$ is methyl.

The process according to the invention is suitable preferably for the preparation of compounds of formula I wherein $R^1$ is $C_1$-$C_4$haloalkyl; $R^2$ is $C_1$-$C_6$ alkyl; and $R^3$ is methyl or ethyl.

In particular, the process according to the invention is suitable preferably for the preparation of compounds of formula I wherein $R^1$ is difluoromethyl or trifluoromethyl; $R^2$ is methyl or ethyl; and $R^3$ is methyl.

The process according to the invention is especially suitable for the preparation of compounds of formula I wherein $R^1$ is difluoromethyl.

The process according to the invention is very especially suitable for the preparation of compounds of formula I wherein $R^1$ is difluoromethyl; $R^2$ is ethyl and $R^3$ is methyl.

Preferably the compound of formula III is dimethyl sulphate.

Preferably the reaction is carried out in a biphasic solvent system, in particular a liquid-liquid biphasic solvent system, e.g. one comprising water and a water-immiscible organic solvent. The term "water-immiscible" means that when the organic solvent is mixed with water under the conditions of the process according to the invention two separate liquid phases are formed. Suitable organic solvents are optionally halogenated aromatic hydrocarbon solvents, ketone solvents, optionally halogenated hydrocarbon solvents or ether solvents. In said definitions, halogen is generally fluorine, chlorine, bromine and/or iodine, preferably fluorine, bromine and/or chlorine. Preferred solvents are aromatic-based organic solvents, e.g. those containing a phenyl group, and/or ethers. Preferred examples are toluene, xylene, mesitylene, tert-butyl benzene, chlorobenzene, 1,2-dichlorobenzene, decalin, dibutyl ether, dipentyl ether, diphenyl ether and anisole. In some cases, more than one type of solvent may be employed. A mixture of toluene and water or xylene and water is preferably employed as solvent.

When the reaction is performed using a one-phase solvent system, the solvent is preferably an organic solvent as described above, with toluene and xylene, particularly toluene, being preferred.

Preferably the process is performed using a phase transfer catalyst. Suitable phase-transfer catalysts are quaternary phosphonium salts such as, for instance, (alkyl)$_4$P$^+$Hal$^-$, (aryl)$_4$P$^+$Hal$^-$, alkylaryl-P$^+$Hal$^-$, etc. (Hal referring to halide) or quanternary ammonium salts such as, for instance, tetraalkylammonium halides or hydroxides, tetraarylammonium halides or hydroxides, alkylarylammonium halides or hydroxides, etc., which are described for example in C. M. Starks, C. L. Liotta, M. C. Halpern, Phase Transfer Catalysis; Chapman & Hall; New York, 1994.

Preferably, the phase transfer catalyst is selected from 1,4-diazabicyclo[2,2,2]octane (DABCO), tetramethylammonium chloride (TMAC), tricaprylylmethylammonium chloride (Aliquat 336®), tetrabutylammonium chloride (TBAC), tetrabutylammonium bromide (TBAB) and triphenylphosphonium chloride (TPPC).

The phase transfer catalyst is generally employed in the inventive reaction in an amount of from 0.001 to 0.1 mol per mol of compound of formula I. An amount of from 0.01 to 0.05 mol per mol of compounds of formula I is preferred.

Preferably the process is performed in the presence of a base. The base may be any suitable base. Suitable bases are, for example, hydroxides and carbonates, e.g. alkali hydroxides and alkali carbonates. Preferred examples are for instance, sodium hydroxide, potassium hydroxide, etc. or alkali carbonate, for instance, sodium carbonate, potassium carbonate, etc. Sodium hydroxide is preferably employed as the base. The base is preferably provided in an amount such that the pH is 9 to13, preferably 9.5 to 12.5 more preferably 10.5 to 12, most preferably 10.8 to 11.5.

The reaction according to the invention is preferably carried out in a temperature range of from 0° C. to 100° C., preferably 10° C. to 50° C., especially from 15° C. to 50° C.

In the reactions according to the invention, compounds of formula III are usually used in equimolar amounts or in excess relative to compounds of formula II, preferably in an up to 10-fold molar excess, especially in an up to 5-fold molar excess, more especially in an equimolar to 2-fold molar excess, even more especially in an equimolar to 1.5 molar excess. Most preferred is a slight molar excess of compound of formula III relative to the compounds of formula II, e.g. from more than equimolar to 1.4 molar excess, e.g. 1.05 to 1.3 molar excess.

The process according to the invention is very especially suitable for the preparation of compounds of formula I wherein R$^1$ is difluoromethyl, R$^2$ is ethyl and R$^3$ is methyl, by reaction of a compound of formula II wherein R$^1$ is difluoromethyl and R$^2$ is ethyl with a compound of formula III wherein R$^3$ is methyl, in a biphasic solvent system, in the presence of base and phase transfer catalyst.

In particular, the process according to the invention is very especially suitable for the preparation of compounds of formula I wherein R$^1$ is difluoromethyl, R$^2$ is ethyl and R$^3$ is methyl, by reaction of a compound of formula II wherein R$^1$ is difluoromethyl and R$^2$ is ethyl with a compound of formula III wherein R$^3$ is methyl, in a temperature range of from 0° C. to 100° C., in a biphasic solvent system, in the presence of base and phase transfer catalyst, the compound of formula III being used in an equimolar to 2-fold excess relative to the compound of formula II.

The compounds of formula II are known or can be prepared analogously to processes known in the literature. For example, such compounds can be prepared from the 3-oxo-carboxylic acid esters on which they are based by means of a two-step synthesis by reaction with trimethyl orthoformate and subsequent reaction with hydrazine. Such reactions are described, for example, in JP-2000-044541. A further synthesis route for the preparation of compounds of formula II is described in JP-2001-322983, wherein, for example, ethyl 3-trifluoromethylpyrazole-4-carboxylate is prepared starting from ethyl 3-chloro-4,4,4-trifluoro-2-formyl-2-butenoic acid ester by reaction with hydrazine. Compounds of formula III are commercially available.

The present invention relates also to the use of compounds of formula III in the regioselective alkylation of compounds of formula II. The present invention relates also to a process for the regioselective alkylation of compounds of formula II, wherein a compound of formula III is used as alkylating agent.

Table 1 shows examples of compounds of formula I of the invention.

TABLE 1

Compounds of formula I:

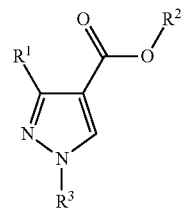

(I)

| Comp. No. | R$_1$ | R$_2$ | R$_3$ |
|---|---|---|---|
| A1 | CF$_2$H | CH$_2$CH$_3$ | CH$_3$ |
| A2 | CF$_2$H | CH$_3$ | CH$_3$ |
| A3 | CF$_2$H | CH$_3$ | CH$_2$CH$_3$ |
| A4 | CF$_2$H | CH$_2$CH$_3$ | CH$_2$CH$_3$ |
| A5 | CF$_3$ | CH$_2$CH$_3$ | CH$_3$ |
| A6 | CF$_3$ | CH$_3$ | CH$_3$ |
| A7 | CF$_3$ | CH$_3$ | CH$_2$CH$_3$ |
| A8 | CF$_3$ | CH$_2$CH$_3$ | CH$_2$CH$_3$ |

The present invention makes it possible for substituted pyrazoles to be alkylated in a controlled manner in a high yield, with a high degree of regioselectivity and at low cost.

A further advantage of the present invention is that the desired product ethyl 3-(difluoromethyl)-1-methyl-1H-pyrazole-4-carboxylate (DFPE) can be purified by sequential vacuum distillation, first to remove undesired ethyl 5-(difluoromethyl)-1-methyl-1H-pyrazole-4-carboxylate (iso-DFPE), then DFPE. It can also be purified by crystallization.

Accordingly, the process may include the step of separating by distillation the compound of formula I from any compound of formula IV:

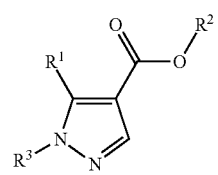

(IV)

wherein R$^1$, R$^2$ and R$^3$ are as defined above;
that has formed in the process.

The process may comprise purifying the compound of formula I, e.g. by crystallisation.

The starting materials for the process of the present invention are distinguished by ready accessibility and ease of handling and are also inexpensive.

In a further aspect the invention provides a process for the preparation of compounds of formula I:

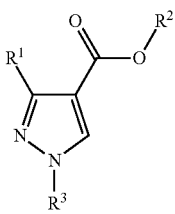
(I)

wherein $R^1$ is $C_1$-$C_4$haloalkyl;
$R^2$ is optionally substituted alkyl, optionally substituted aryl or optionally substituted heteroaryl; and
$R^3$ is methyl or ethyl;
comprising
a) reacting a compound of formula V:

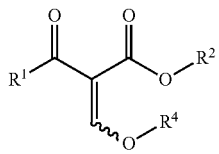
(V)

wherein $R^1$ and $R^2$ are as defined for the compound of formula I and $R^4$ is hydrogen, optionally substituted alkyl, optionally substituted aryl or optionally substituted heteroaryl;
with hydrazine in the presence of water and a water-immiscible organic solvent to form a compound of formula II:

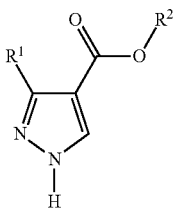
(II)

wherein $R^1$ and $R^2$ are as defined for the compound of formula I; and
b) reacting the compound of formula II with an alkylating agent in situ to produce the compound of formula I.

Preferred definitions of $R^1$, $R^2$, $R^3$ are the same as those given above. Most preferably $R^1$ is difluoromethyl, $R^2$ is $C_1$-$C_6$ alkyl e.g. ethyl, $R^4$ is hydrogen or $C_1$-$C_6$ alkyl, more preferably $C_1$-$C_6$ alkyl, e.g. ethyl, and $R^3$ is methyl.

For example, reacting the compound of formula II with an alkylating agent in situ means that the compound of formula II is not isolated from the crude reaction mixture prior to reaction with the alkylating agent. Accordingly, the preparation of a compound of formula I from the compound of formula II may be a "one-pot" reaction, e.g. step b) may be performed after step a) in the same vessel. This simplifies the plant requirements for the process.

Following the reaction of the compound of formula V with hydrazine, the organic phase will contain the compound of formula I. The organic phase may be separated from the aqueous phase prior to reacting the compound of formula II with an alklyating agent. The alkylating agent may then be added to the organic phase. The alkylation reaction may also be performed using a biphasic solvent system.

The alkylating agent may be selected from known alkylating agents. Suitable alkylating agents may include for example alkyl phosphates, alkyl phosphonates, an alkyl phosphites, alkyl sulphates and alkyl carbonates, for example a compound of formula III, VI, VII or VIII:

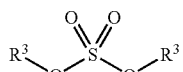
(III)

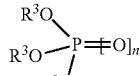
(VI)

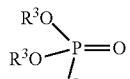
(VII)

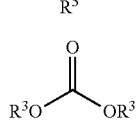
(VIII)

wherein
$R^3$ is methyl or ethyl;
$R^5$ is hydrogen, optionally substituted alkyl, optionally substituted aryl or optionally substituted heteroaryl, preferably hydrogen or $C_1$-$C_6$ alkyl, e.g. ethyl; and
n is 0 or 1.

Preferred alkylating reagents are compounds of formula III and VI, particularly alkylphosphates and alkylsulphonates. Dimethylsulphate and trimethylphosphate are particularly preferred.

In step a) hydrazine can be used in equimolar amounts, in sub-equimolar amounts or in excess relative to compounds of formula V, preferably hydrazine is used in slight excess relative to compounds of formula V. Thus the molar ratio of hydrazine:compound of formula V is preferably from 1:0.8 to 1:1.2, preferably 1:1.1. Hydrazine may be used in the form of an aqueous solution.

Preferred organic solvents in step a) are as described above for alkylation of compounds of formula II with compounds of formula III.

Process step a) is preferably carried out in a temperature range from −20° C. to 50° C., preferably from 0° C. to 50° C., especially from 5° C. to 25° C.

The reaction time for process step a) is generally from 15 minutes to 48 hours, preferably 15 minutes to 18 hours, more preferably 15 minutes to 5 hours or from 1 to 5 hours. Said step can be carried out at normal, elevated or reduced pressure. In one embodiment, said step is carried out at normal pressure.

An example of step a) is a process step comprising: preparing a solution comprising hydrazine or hydrazine hydrate and an organic solvent, preparing a suspension/solution of the compound of formula V in the organic solvent, and mixing the solution and the suspension or both solutions. The solution comprising hydrazine can be added to the suspension/solution of the compound of formula V in the organic solvent or vice versa. In one embodiment, the suspension/solution of the compound of formula V in the organic solvent is added to the solution comprising hydrazine.

Step b) may be performed under similar conditions as described above for the reaction of compounds of formula II with compounds of formula III. Preferably step b) is performed according using a compound of formula III according to the invention as described above.

Compounds of formula V occur in two isomers with regard to the double bond substituted by the alkoxy group —O—$R_2$: the E- and the Z-isomer. Both isomers or mixtures thereof can be used in the processes according to the invention.

Compounds of formula V are described for example in WO 2008/113447.

In a further aspect the invention provides a process for the preparation of a compound of formula I:

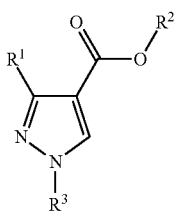
(I)

wherein $R^1$ is $C_1$-$C_4$haloalkyl;
$R^2$ is optionally substituted alkyl, optionally substituted aryl or optionally substituted heteroaryl; and
$R^3$ is methyl or ethyl;
wherein a compound of formula II:

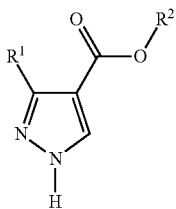
(II)

wherein $R^1$ and $R^2$ are as defined for the compound of formula I;
is reacted with an alkylating agent in a liquid-liquid biphasic solvent system.

Preferably the biphasic solvent system is water and a water-immiscible organic solvent, e.g. as described above.

The alkylating agent may be selected from known alkylating agents. Suitable alkylating agents may include for example alkyl phosphates, alkyl phosphonates, an alkyl phosphites, alkyl sulphates and alkyl carbonates, for example a compound of formula III, VI, VII or VIII:

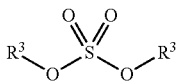
(III)

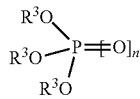
(VI)

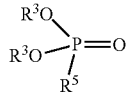
(VII)

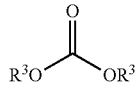
(VIII)

wherein
$R^3$ is methyl or ethyl;
$R^5$ is hydrogen, optionally substituted alkyl, optionally substituted aryl or optionally substituted heteroaryl, preferably hydrogen or $C_1$-$C_6$ alkyl, e.g. ethyl; and
n is 0 or 1.

Preferably the alkylating agent is a compound of formula III, VI or VII, more preferably a compound of formula III. More preferred alkylating reagents are compounds of formula III and VI, particularly alkylphosphates and alkylsulphonates. Dimethylsulphate and trimethylphosphate are particularly preferred.

In a further aspect the invention provides a process for the preparation of a compound of formula IX:

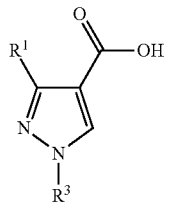
(IX)

wherein $R^1$ is $C_1$-$C_4$haloalkyl and $R^3$ is methyl or ethyl; comprising hydrolysing a compound of formula I, prepared as described above.

Hydrolysis of the compound of formula I may be achieved by performing the steps:
i) saponifying that compound in situ leading to the formation of a compound of formula IX by
ii) adding a base to form the anion of the compound of formula IX;
ii') adding an acid to form the compound of formula IX;
e.g. as described in WO 2008/145257.

In a further aspect the invention provides a process for the preparation of a compound of formula X:

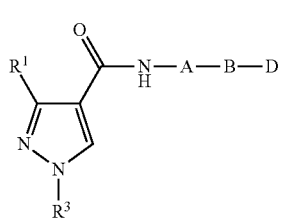
(X)

wherein R¹ is $C_1$-$C_4$haloalkyl and R³ is methyl or ethyl;
A is thienyl, phenyl, or ethylene each optionally substituted by one to three groups independently selected from halogen, methyl and methoxy,
B is a direct bond, cyclopropylene, an annelated bicyclo[2.2.1]heptane- or bicyclo[2.2.1]heptene ring,
D is hydrogen, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_1$-$C_6$ alkylidene, $C_1$-$C_6$ haloalkylidene, phenyl or phenyl optionally substituted by one to three substituents independently selected from halogen and trihalomethylthio;
comprising providing a compound of formula IX:

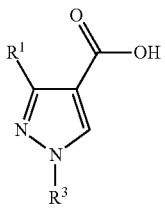

(IX)

wherein R¹ is $C_1$-$C_4$haloalkyl and R³ is methyl or ethyl; according to the processes described above; and
reacting the compound of formula IX or the corresponding acid-halide with a compound of formula XI:

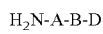

(XI)

wherein A, B and D are as defined for the compound of formula X.

The compound of formula X is preferably a compound of formula XII (Isopyrazam), a compound of formula XIII (Sedaxane), a compound of formula XIV, a compound of formula XV (Penthiopyrad), a compound of formula XVI (Bixafen), a compound of formula XVII (Fluxapyroxad), a compound of formula XVIII, or a compound of formula XIX:

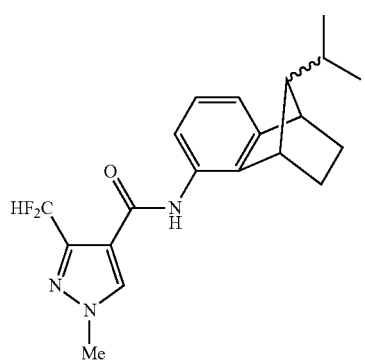

(XII)

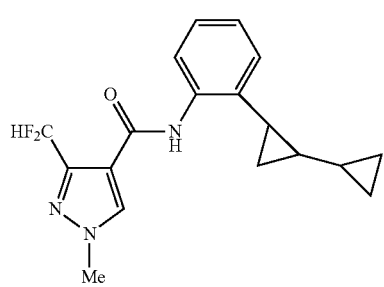

(XIII)

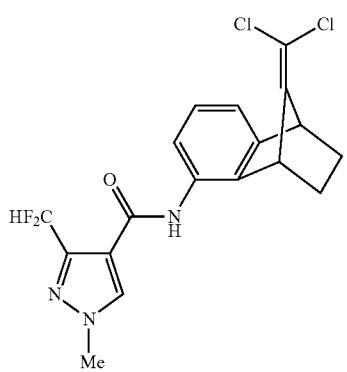

(XIV)

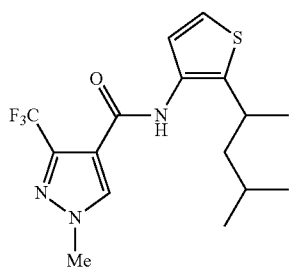

(XV)

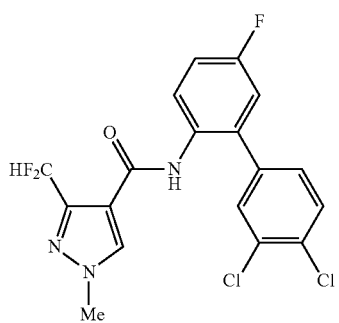

(XVI)

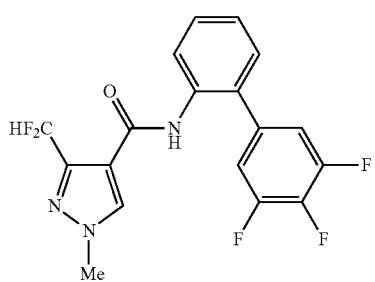

(XVII)

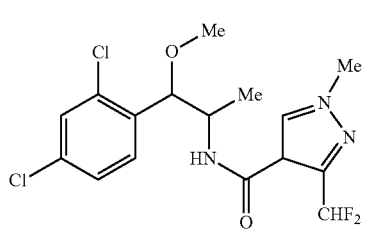

(XVIII)

(XIX)

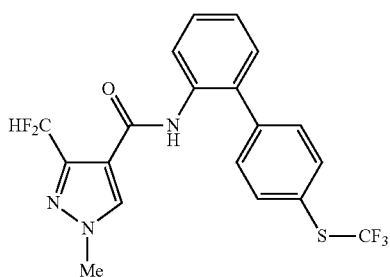

The step of reacting the compound of formula IX or the corresponding acid-halide with a compound of formula XI may be performed according to known methods, e.g. as described in WO 2004/035589 or WO 2009/135860. For example, the compound of formula I may be treated with a halogenating agent, such as thionyl chloride, oxalyl chloride, phosgene, $SF_4$, DAST, deoxofluor or thionylbromide to provide the acid-halogen, e.g. the acid chloride, which may then be reacted with the compound of formula XI in the presence of a suitable base, e.g. LiOH, KOH, NaOH, $NEt_3$, $NaHCO_3$, $KHCO_3$, $Na_2CO_3$ or $K_2CO_3$, e.g. in a solvent such as toluene, xylenes, dichloromethane, ethyl acetate or DMF, e.g. at −10° C. to 30° C.

Isopyrazam, Sedaxane, Penthiopyrad, Fluxapyroxad and Bixafen are known fungicides. The compound of formula XIV is known, e.g. from WO 2007/048556, the compound of formula XVIII is known e.g. from WO 2010/000612, the compound of formula XIX is known e.g. from WO 2008/053044.

EXAMPLES

Example 1

Preparation of ethyl 3-(difluoromethyl)-1-methyl-1H-pyrazole-4-carboxylate (DFPE) Using a Biphasic Solvent System Example 1a 19 g (0.10 mol) of ethyl 3-difluoromethylpyrazole-4-carboxylate, toluene (60 ml), water (70 ml), and tetramethylammonium chloride (0.2 g) were mixed. 4.6 g of 25% aqueous sodium hydroxide (0.03 mol) was added while stirring. The mixture was cooled to 15° C. Then, over the course of 2 hours, 15.1 g of dimethyl sulphate (0.12 mol) and 11.2 g of additional sodium hydroxide (0.07 mol) were fed simultaneously while maintaining the pH at 10.8 to 11.0 and pot temperature at 15° C. The reaction mixture was allowed to stir at the same temperature while maintaining the pH at 10.8-11.0 by feeding additional sodium hydroxide solution. The bottom aqueous phase was separated off. The organic phase was concentrated in vacuo to give 20.0 g of crude product as a 70:30 mixture of DFPE and ethyl 5-(difluoromethyl)-1-methyl-1H-pyrazole-4-carboxylate (iso-DFPE).

The desired DFPE product was purified by vacuum distillation at 95° C./5 mbar to remove undesired iso-DFPE, followed by recrystallization in methanol-water. 11.8 g (99.9%, 0.06 mol) of DFPE was obtained. DFPE can also be isolated and purified by vacuum distillation at 110° C./1 mbar.

Example 1b 19 g (0.10 mol) of ethyl 3-difluoromethylpyrazole-4-carboxylate, toluene (60 ml), water 30 (35 ml), and tetrabutylammonium bromide (0.2 g) were mixed. 4.6 g of 25% aqueous sodium hydroxide (0.03 mol) was added while stirring. The mixture was cooled to 15° C. Then, over the course of 2 hours, 15.1 g of dimethyl sulphate (0.12 mol) and 11.2 g of additional sodium hydroxide (0.07 mol) were fed simultaneously while maintaining the pH at 10.8 to 11.0 and pot temperature at 15° C. The reaction mixture was allowed to stir at the same temperature while maintaining the pH at 10.8-11.0 by feeding additional sodium hydroxide solution. The bottom aqueous phase was separated off. GC analysis of the organic phase showed that it contains 20.0 g of crude product as a 70:30 mixture of DFPE and ethyl 5-(difluoromethyl)-1-methyl-1H-pyrazole-4-carboxylate (iso-DFPE). The combined yield is 95%.

Example 1c 63.8 g (0.336 mol) of ethyl 3-difluoromethylpyrazole-4-carboxylate, toluene (260 ml), and water (52 ml) were mixed. 18.0 g of 25% aqueous sodium hydroxide (0.112 mol) was added while stirring. Then, over the course of 2 hours, 49.6 g of dimethyl sulphate (0.390 mol) and 45.3 g of additional sodium hydroxide (0.283 mol) were fed simultaneously while maintaining the pH at 11.3 to 11.6 and pot temperature at 25° C. The reaction mixture was allowed to stir at the same temperature for 2 hours while maintaining the pH at 11.3-11.6 by feeding additional sodium hydroxide solution. The bottom aqueous phase was separated off. GC analysis of the organic phase showed that it contains 64.5 g of crude product as a 62:38 mixture of DFPE and ethyl 5-(difluoromethyl)-1-methyl-1H-pyrazole-4-carboxylate (iso-DFPE). The combined yield is 94%.

Example 2

Preparation of ethyl 3-(difluoromethyl)-1-methyl-1H-pyrazole-4-carboxylate (DFPE) Using a Monophasic Solvent System Example 2a 31.9 g (0.17 mol) of ethyl 3-difluoromethylpyrazole-4-carboxylate, toluene (110 ml), 34.8 g of potassium carbonate (0.5 mol) and tetramethylammonium chloride (1.2 g) were mixed. Then, over the course of 2 hours, 26.4 g of dimethyl sulphate (0.21 mol) was fed while maintaining the pot temperature at 25° C. The reaction mixture was allowed to stir at the same temperature for additional 2 hours. Water (200 g) was added to dissolve the solid by-products. The bottom aqueous phase was separated off. GC analysis of the organic phase showed that it contains 32.3 g of crude product as a 58:42 mixture of DFPE and ethyl 5-(difluoromethyl)-1-methyl-1H-pyrazole-4-carboxylate (iso-DFPE). The combined yield is 95%.

Example 2b 31.9 g (0.17 mol) of ethyl 3-difluoromethylpyrazole-4-carboxylate, toluene (110 ml) and 34.8 g of potassium carbonate (0.5 mol) were mixed. Then, over the course of 2 hours, 26.4 g of dimethyl sulphate (0.21 mol) was fed while maintaining the pot temperature at 25° C. The reaction mixture was allowed to stir at the same temperature for additional 2 hours. Water (200 g) was added to dissolve the solid by-products. The bottom aqueous phase was separated off. GC analysis of the organic phase showed that it contains 32.2 g of crude product as a 58:42 mixture of DFPE and ethyl 5-(difluoromethyl)-1-methyl-1H-pyrazole-4-carboxylate (iso-DFPE). The combined yield is 95%.

Example 3

One-Pot Preparation of ethyl 3-(difluoromethyl)-1-methyl-1H-pyrazole-4-carboxylate (DFPE)

A mixture of toluene (450 ml) and hydrazine monohydrate (48.8 g, 0.98 mol) was stirred at 15-20° C. 2-[1-Ethoxy-meth-(Z)-ylidene]-4,4-difluoro-3-oxo-butyric acid ethyl ester (175.3 g, 91.5% strength, 0.72 mol) was fed over 2 hours via a syringe pump while maintaining the temperature at 15-20° C. The reaction mass was held at 15-20° C. for additional 30 minutes to complete the reaction.

The reaction mixture was then warmed to 30° C. to dissolve the solid product. The bottom aqueous phase was decanted off. The organic phase was washed with 2% HCl (50 ml) to remove residual hydrazine. The two aqueous phases were combined and extracted with toluene (50 ml). The toluene extract contains additional 3-4% yield of ethyl 3-difluoromethylpyrazole-4-carboxylate and was combined with the product solution.

The toluene solution of crude ethyl 3-difluoromethylpyrazole-4-carboxylate was stirred and cooled to 20° C. Water (260 ml), tetramethylammonium chloride (10% aqueous solution, 15.0 g), and 25% NaOH solution (36-60 g) were added in sequence. Dimethyl sulphate (99.5%, 94.5 g, 0.75 mol) and additional 25% NaOH were fed simultaneously over 2 hours at 20° C. while maintaining the pH between 10.5 and 12.0. After 2 hours post reaction, the bottom aqueous phase was separated off.

After solvent was evaporated off, the crude reaction mass was vacuum distilled to afford 46.5 g of ethyl 5-(difluoromethyl)-1-methyl-1H-pyrazole-4-carboxylate (iso-DFPE) as a distillation fraction. The distillation residue contains 86.3 g of DFPE and less than 1.0 g of iso-DFPE, and can be hydrolyzed directly to produce the corresponding acid.

What is claimed is:

1. A process for the preparation of a compound of formula I:

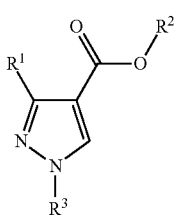

(I)

wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
wherein a compound of formula II:

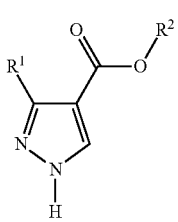

(II)

wherein $R^1$ and $R^2$ are as defined for the compound of formula I;
is reacted with a compound of formula III:

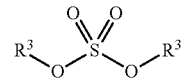

(III)

wherein $R^3$ is as defined for the compound of formula I.

2. A process according to claim 1, wherein the reaction is performed in a liquid-liquid biphasic solvent system.

3. A process according to claim 2, wherein the biphasic solvent system comprises water and a water-immiscible organic solvent.

4. A process according to claim 2, wherein the reaction is performed in the presence of a phase transfer catalyst.

5. A process according to claim 4, wherein the phase transfer catalyst is a quaternary phosphonium salt or a quanternary ammonium salt.

6. A process according to claim 4, wherein the phase transfer catalyst is selected from 1,4-diazabicyclo[2,2,2]octane (DABCO), tetramethylammonium chloride (TMAC), tricaprylylmethylammonium chloride (Aliquat 336®), tetrabutylammonium chloride (TBAC), tetrabutylammonium bromide (TBAB) and triphenylphosphonium chloride (TPPC).

7. A process according to claim 1 wherein the compound of formula III is present in an amount which is equimolar to 2-fold molar excess relative to the compound of formula II.

8. A process according to claim 1, wherein the reaction is carried out in the presence of a base.

9. A process according to claim 8, wherein the base is a hydroxide or a carbonate.

10. A process according to claim 1, wherein the process comprises the step of separating by distillation the compound of formula I from any compound of formula IV:

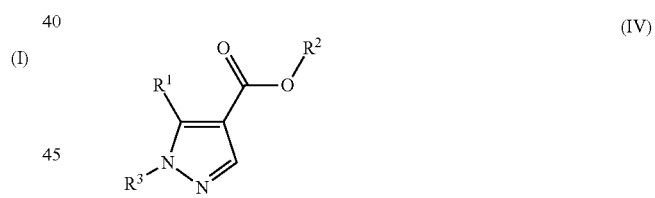

(IV)

wherein $R^1$, $R^2$ and $R^3$ are as defined for the compound of formula I in claim 1;
that has formed in the process according to claim 1.

11. A process according to claim 1, wherein $R^2$ is $C_1$-$C_6$ alkyl.

12. A process for the regioselective alkylation of a compound of formula II:

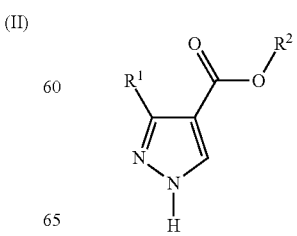

(II)

wherein
R$^1$ is C$_1$-C$_4$haloalkyl; and
R$^2$ is optionally substituted alkyl, optionally substituted aryl or optionally substituted heteroaryl;
wherein a compound of formula III:

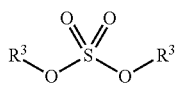

(III)

wherein R$^3$ is methyl or ethyl;
is used as the alkylating agent.

13. A process for the preparation of a compound of formula I:

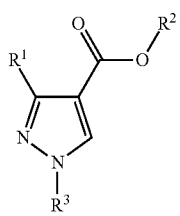

(I)

wherein R$^1$ is C$_1$-C$_4$haloalkyl;
R$^2$ is optionally substituted alkyl, optionally substituted aryl or optionally substituted heteroaryl; and
R$^3$ is methyl or ethyl;
comprising
a) reacting a compound of formula V:

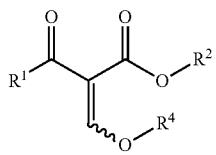

(V)

wherein R$^1$ and R$^2$ are as defined for the compound of formula I and R$^4$ is hydrogen, optionally substituted alkyl, optionally substituted aryl or optionally substituted heteroaryl;
with hydrazine in the presence of water and a water-immiscible organic solvent to form a compound of formula II:

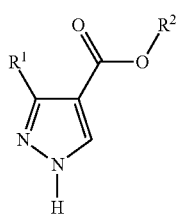

(II)

wherein R$^1$ and R$^2$ are as defined for the compound of formula I; and b) reacting the compound of formula II with an alkylating agent in situ to produce the compound of formula I, wherein the alkylating agent is a compound of formula (III)

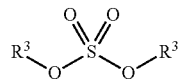

(III)

wherein R$^3$ is methyl or ethyl.

14. A process according to claim 13, wherein after step a) the organic phase is separated from the aqueous phase prior to reacting the compound of formula II with an alklyating agent in step b).

15. A process according to claim 13, wherein the water-immiscible organic solvent is an aromatic-based solvent and/or an ether.

16. A process according to claim 13, wherein the alkylating agent is selected from dimethylsulphate and trimethylphosphate.

17. A process for the preparation of a compound of formula I:

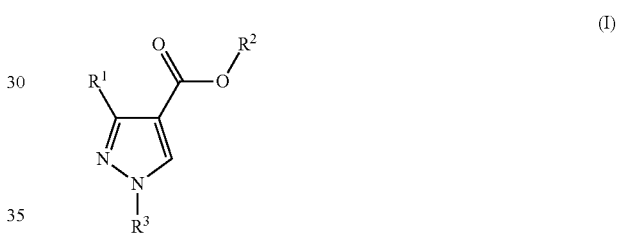

(I)

wherein R$^1$ is C$_1$-C$_4$haloalkyl;
R$^2$ is optionally substituted alkyl, optionally substituted aryl or optionally substituted heteroaryl; and
R$^3$ is methyl or ethyl;
wherein a compound of formula II:

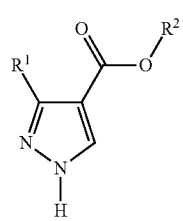

(II)

wherein R$^1$ and R$^2$ are as defined for the compound of formula I;
is reacted with an alkylating agent in a liquid-liquid biphasic solvent system, wherein the alkylating agent is a compound of formula (III)

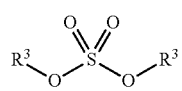

(III)

wherein R$^3$ is methyl or ethyl.

18. A process according to claim 17, wherein the biphasic solvent system comprises water and a water-immiscible organic solvent.

19. A process according to claim 17, wherein the alkylating agent is selected from dimethylsulphate and trimethylphosphate.

20. A process for the preparation of a compound of formula IX:

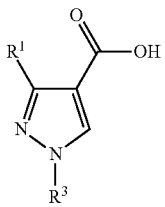

(IX)

wherein $R^1$ is $C_1$-$C_4$haloalkyl and $R^3$ is methyl or ethyl; comprising hydrolysing a compound of formula I, prepared according to a method as defined in claim 1.

21. A process for the preparation of a compound of formula X:

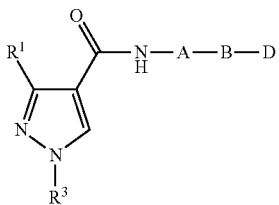

(X)

wherein $R^1$ is $C_1$-$C_4$haloalkyl;
$R^3$ is methyl or ethyl;
A is thienyl, phenyl, or ethylene each optionally substituted by one to three groups independently selected from halogen, methyl and methoxy,
B is a direct bond, cyclopropylene, an annelated bicyclo[2.2.1]heptane- or bicyclo[2.2.1]heptene ring,
D is hydrogen, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_1$-$C_6$ alkylidene, $C_1$-$C_6$ haloalkylidene, phenyl or phenyl optionally substituted by one to three substituents independently selected from halogen and trihalomethylthio;
comprising providing a compound of formula IX:

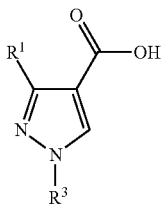

(IX)

wherein $R^1$ is $C_1$-$C_4$haloalkyl and $R^3$ is methyl or ethyl; according to the process as defined in claim 20; and
reacting the compound of formula IX or the corresponding acid-halide with a compound of formula XI:

$H_2N$-A-B-D          (XI)

wherein A, B and D are as defined for the compound of formula X.

22. A process according to claim 21, wherein the compound of formula X is a compound of formula XII (Isopyrazam), a compound of formula XIII (Sedaxane), a compound of formula XIV, a compound of formula XV (Penthiopyrad), a compound of formula XVI (Bixafen), a compound of formula XVII (Fluxapyroxad), a compound of formula XVIII, or a compound of formula XIX:

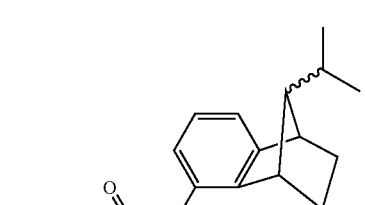

(XII)

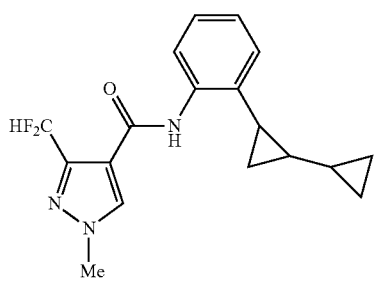

(XIII)

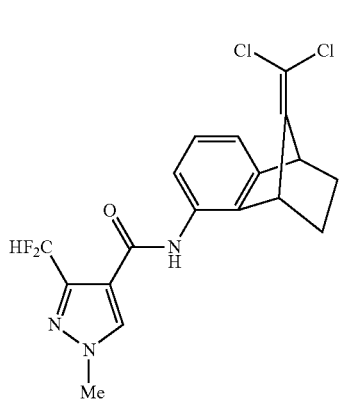

(XIV)

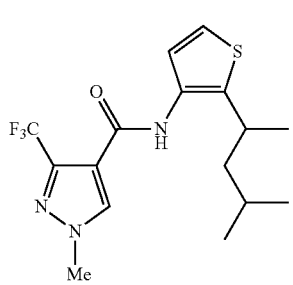

(XV)

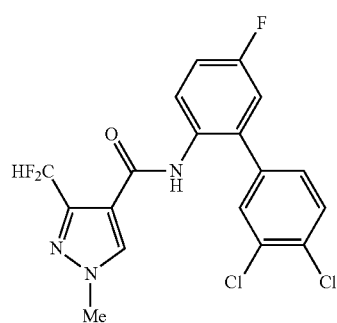 (XVI)
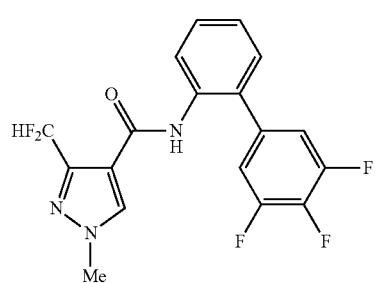 (XVII)
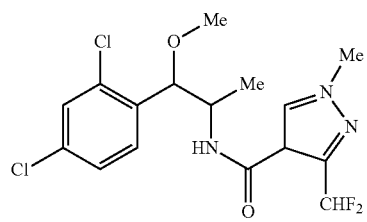 (XVIII)
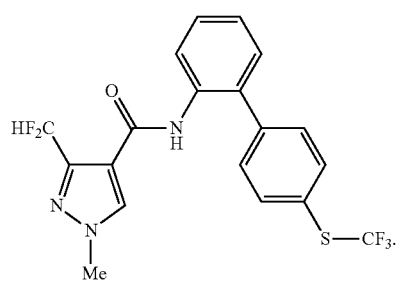 (XIX)
\* \* \* \* \*